United States Patent
Hoopes

(10) Patent No.: US 6,870,081 B2
(45) Date of Patent: Mar. 22, 2005

(54) POTATO CULTIVAR FL1900

(75) Inventor: Robert W. Hoopes, Rhinelander, WI (US)

(73) Assignee: Recot Inc., Pleasanton, CA (US)

( * ) Notice: Subject to any disclaimer, the term of this patent is extended or adjusted under 35 U.S.C. 154(b) by 6 days.

(21) Appl. No.: 09/875,282

(22) Filed: Jun. 7, 2001

(65) Prior Publication Data

US 2002/0042936 A1 Apr. 11, 2002

Related U.S. Application Data

(60) Provisional application No. 60/210,131, filed on Jun. 7, 2000.

(51) Int. Cl.$^7$ .............................. A01H 5/00; A01H 1/00; C12N 15/82; C12N 15/87; C12N 5/00

(52) U.S. Cl. .................... 800/317.2; 800/260; 800/278; 800/293; 800/294; 800/295; 800/298; 435/419; 435/417; 435/429; 435/430; 435/469; 435/459

(58) Field of Search .............................. 800/317.2, 260, 800/263, 265, 266, 267, 278, 279, 280, 284, 285, 287, 288, 290, 295, 300, 301, 302; 435/430, 430.1, 410, 413, 417, 418

(56) References Cited

U.S. PATENT DOCUMENTS

| | | | | |
|---|---|---|---|---|
| 4,696,674 A | * | 9/1987 | Cipar et al. ..................... | 800/1 |
| 5,434,342 A | * | 7/1995 | Cipar et al. .................. | 800/200 |
| 5,523,520 A | * | 6/1996 | Hunsperger et al. ........ | 800/200 |

OTHER PUBLICATIONS

Bennetzen et al. 1992. Approaches and progress in the molecular cloning of plant disease resistance genes.pp 99–124, In: Genetic Engineering, vol. 14. Eds. J.K. Setlow. Plenum Press, NY.*
Chase et al. 1992. Michigold: a yellow–fleshed potato cultivar for fresh market. Am. Potato J. 69(10):629–634.*
DeBolle et al. 1996. antimicrobial peptides from Mirabilis jalapa and Amarantus cuadatus: espression, processing, localization and biological activity in transgenic tobacco. Plant Molec. biol. 31:993–1008.*
Eshed et al. 1996. Less–than–additive epistatic interactions of quantitative trait loci in tomato. Geneetics 143:1807–1817.*
Genet et al. 1995. Gladiator: a new potato cultivar with high resistance to potato cyst nematode adn powdery scab suitable for french fries and fresh market. New Zealand J. Crop and hort. Sci. 23:105–107.*

Goth et al. Relative resistance of thepotato cultivar Krantz to common scab cuased by streptomyces scabies as determined by cluser analysis. Am potato J. 72(7):505–511.*
Hemmat et al. 1998. Molecular markers for the scab resistance (Vf) region in apple. J. Amer. Soc. Hort. Sci. 123(6):992–996.*
Kraft et al. 2000. Linkage disequilibrium and fingerprinting in sugar beet. Thero Appl. Genet. 101:323–326.*
Lopez et al. 1987. Genotype x environment interactions, correlations, and combing ability for six traits in potato. Am. Potato J. 64(8):447.*
Lynch et al. 1994. AC Ptarmigan: an early maturing potato cultivar with good chipping and fresh market quality. Am. Potato J. 71(6)387–393.*
Michelmore et al. 1991. identification of markers linked to disease–resistance genes by bulked segregant analysis: a rapid method to detect markers in specific genomic regions byusing segregating populations. PNAS(USA) 88:9828–9832.*
Pang et al 1992. Expression of a gene encoding a scorpion insectotoxin pepetide in yeast, bacteria and plants. ene 116:165–172.*
Sinha et al 1992. Differences in sugars, chip color, specific gravity, and yiled of selected potato cultivars grown in Michigan. Am. Potato J. 69(6):385–387.*
Thisll et al. 1995. A breeding method for accelerated development of cold chipping clones in potato. Euphytica 84:73–80.*
VanOoijen et al. 1996. an RFLP linkage map of Lycopersion esculaentum. Theor. Appl. Genet. 89:1007–1013.*
Kraft et al, 2000, Theoretical Applied Genetics 101:323–326.*
Eshed et al, 1996, Genetics 143:1807–1817.*

* cited by examiner

Primary Examiner—Anne Marie Grunberg
(74) Attorney, Agent, or Firm—Jondle & Associates P.C.

(57) ABSTRACT

A novel potato cultivar of the genus and species *Solanum tuberosum*, designated FL1900, is disclosed. The invention relates to the tubers of potato variety FL1900, to the plants of potato variety FL1900, to the seeds of potato variety and to methods for producing hybrid potato variety. The invention further relates to potato variety tubers, seeds and plants produced by crossing the potato variety FL1900 with another potato plant, and to Single Gene Converted plants.

11 Claims, No Drawings

POTATO CULTIVAR FL1900

BACKGROUND OF THE INVENTION

This application claims priority from provisional application No. 60/210,131, filed Jun. 7, 2000.

The present invention relates to a novel potato variety and to the tubers, plants, plant parts, tissue culture and seeds produced by that potato variety.

The publications and other materials used herein to illuminate the background of the invention and, in particular cases, to provide additional details respecting the practice, are incorporated by reference and for convenience, are referenced in the following text by author and date and are listed alphabetically by author in the appended bibliography.

The potato is the world's fourth most important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C.

To keep the potato industry growing to meet the needs of the consuming public, substantial research and development efforts are devoted to the modernization of planting and harvesting of fields and processing of potatoes, and to the development of economically advantageous potato varieties. Through crossbreeding of potatoes, researchers hope to obtain potatoes with the desirable characteristics of good processability, high solids content, high yield, resistance to diseases and pests and adaptability to various growing areas and conditions.

The U.S. acreage planted in potatoes has declined since the 1960s and 1970s, and this decline, coupled with increasing consumption, must be offset by higher useable yields. In some areas, diseases and pests damage crops despite the use of herbicides and pesticides. The problem of the golden nematode in the United States, presently endemic to portions of New York State, is one example of the destruction to susceptible potato varieties. Potato varieties with high yields, disease resistance and adaptability to new environments can eliminate many problems for the potato grower and provide more plentiful and economical products to the consumers.

For the potato chip processing industry, potatoes having high solids content, good shipping qualities and good finished chip color can increase production volumes and efficiencies and product acceptability. Potato varieties which yield low-solids tubers result in unnecessary energy usage during the frying process. Moreover, as solids content increases, the oil content of fried products decreases, which is a favorable improvement. Potato varieties in the warm southern tier of states are most in need of solids improvement overall, while those varieties grown and stored in the colder northern tier of states are most in need of the ability to recondition after cool or cold storage to increase their value for use in the potato chip industry. Reconditioning is necessary to elevate the temperature of the potatoes after cold storage and before further processing.

The research leading to potato varieties which combine the advantageous characteristics referred to above is largely empirical. This research requires large investments of time, manpower, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques continue with the controlled pollination of parental clones. Typically, pollen is collected in gelatin capsules for later use in pollinating the female parents. Hybrid seeds are sown in greenhouses, and tubers are harvested and retained from thousands of individual seedlings. The next year a single tuber from each resulting seedling is planted in the field, where extreme caution is exercised to avoid the spread of virus and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, eight or more years of planting, harvesting and testing have been invested in attempting to develop the new and improved potato cultivars.

Long-term, controlled-environment storage has been a feature of the northern, principal producing areas for many years. Potatoes harvested by October must be kept in good condition for up to eight months in temperatures that may drop to −30 degrees C. at times and with very low relative humidity in the outside air. Storages are well insulated, not only to prevent heat loss but also to prevent condensation on outside walls. The circulation of air at the required temperature and humidity is automatically controlled depending on the purpose for which the potatoes are being stored. Sprout inhibition is now largely carried out in storage as it has been found to be more satisfactory than the application of maleic hydrazide (MH30) in the field.

Proper testing of new plants should detect any major faults and establish the level of superiority or improvement over current varieties. In addition to showing superior performance, a new variety must be compatible with industry standards or create a new market. The introduction of a new variety will increase costs of the tuber propagator, the grower, processor and consumer; for special advertising and marketing, altered tuber propagation and new product utilization. The testing preceding release of a new variety should take into consideration research and development costs as well as technical superiority of the final variety. Once the varieties that give the best performance have been identified, the tuber can be propagated indefinitely as long as the homogeneity of the variety parent is maintained. For tuber propagated varieties, it must be feasible to produce, store and process potatoes easily and economically.

Thus, there is a continuing need to develop potato cultivars which provide good processability out of storage, with minimal bruising, for manufacturers of potato chips and other potato products and to combine this characteristic with the properties of disease resistance, resistance to pests. The present invention addresses this need by providing the new variety as described herein.

SUMMARY OF THE INVENTION

According to the invention, there is provided a novel potato cultivar of the genus and species, *Solanum*

*tuberosum*, designated FL1900. This invention thus relates to the tubers of potato variety FL1900, the plants and plant parts of potato variety FL1900 and to methods for producing a potato plant produced by crossing the potato variety FL1900 with itself or another potato variety. This invention further relates to hybrid potato seeds and plants produced by crossing the potato variety FL1900 with another potato plant.

In another aspect, the present invention provides for Single Gene Converted plants of FL1900. The single gene transferred may be a dominant or recessive allele. Preferably, the single gene transferred will confer such traits as herbicide resistance, insect resistance, resistance for bacterial, fungal or viral disease, uniformity and increase in concentration of starch and other carbohydrates, decrease in tendency of tuber to bruise and decrease in the rate of conversion of starch to sugars. The single gene transferred may be a naturally occurring gene or a transgene introduced through genetic engineering techniques.

DETAILED DESCRIPTION OF THE INVENTION

A novel potato cultivar of the present invention, which has been designated FL1900, has been obtained by selectively crossbreeding parental clones through several generations. The immediate parents of FL1900 were cultivars designated FL1700 and S440. These parent strains were selected for the ability to be processed into desirably-colored potato chips, high solids, regular round tubers of the right size for chipping, as well as FL1700's resistance to common resistance to common scab and "golden" cyst nematode.

FL1900 cultivar has olive green foliage. This cultivar has medium to late vine growth and violet flowers and produces tubers which are characterized by a white flesh color, a good specific gravity, high solids, and a netted surface and round shape. As a chipping variety, the most appropriate variety with which to compare FL1900 is the commercial cultivar Atlantic. A comparison of FL1900 with Atlantic reveals that FL1900 has medium sized, pentagonal corollar shape, more pronounced waviness on the terminal leaflet, and produces round, white fleshed tubers while Atlantic has fewer florets on each inflorescence and a smaller semi-stellate corollar shape which is lighter in color with much more prominent white streaks on the outer corollar surface, and produces oval, yellow-white fleshed tubers. While both FL1900 and Atlantic have erect growth habit, anthocyanin coloration is more prominent on the stems of FL1900. FL1900 has average yields slightly higher than Atlantic, its solids are higher and its tubers have fewer internal defects than Atlantic. FL1900 is highly resistant to "golden" cyst nematode.

The tubers produced by FL1900 are well-suited for the production of potato chips. A characteristic feature of the tubers is their good specific gravity relative to the standard commercial variety in a production area. The specific gravity generally ranges from about 1.080 to 1.089; however, it will be appreciated that specific gravities can vary substantially depending upon growing conditions and areas. Higher specific gravities are advantageous for chipping and other frying applications, as they reduce the total energy and time required for the frying operation.

In addition to the specific gravity of the tubers of this invention, they also have an advantageous shape for commercial operations. The tubers have shallow eyes, are generally round and lack knobs and other protuberances, as well as deep ridges or convolutions. Accordingly, they are amenable to efficient washing and peeling operations using large-scale automated equipment. Such shapes produce a high quality product with a minimal amount of waste. The tubers have a size and shape which is suited to the manufacture of potato chips. On average, these tubers have an average length of 77.5 millimeters (range: 62–106 millimeters); an average width of 60.6 millimeters (range: 44–75 millimeters); and an average thickness of 45 millimeters (range: 38–53 millimeters) based upon a 100-tuber sample. Of course, the size of the tubers can vary over a relatively wide range depending on growing conditions and locations. The slightly flattened shape of the tubers is advantageous, because it facilitates alignment in the slicing apparatus.

Among the more important characteristics of the potato cultivar of this invention is its resistance to "golden" potato cyst nematode (*Globodera rosto chiensis* race R01). Additionally, it has white flesh and produces attractive chips with higher solids and fewer internal defects than Atlantic.

In addition to the morphological characteristics and disease and pest resistance as described above, the plants of this invention are characterized by their protein "fingerprint" patterns. The protein "fingerprint" is determined by separating tuber proteins on an electrophoretic gel under certain defined conditions. The pattern of the proteins, attributable to their differential mobilities on the electrophoretic gel, have been found to be characteristic of the particular plant involved. This pattern has thus been termed a "fingerprint." Isozyme fingerprints of all available North American potato varieties have revealed that no two varieties have the same pattern for the enzymes tested. (Douches and Ludlam, 1991). The isozyme fingerprint of FL1900 has been established as distinct from that of any other variety tested, including Atlantic (Douches and Ludlam, 1991). These techniques generally involve extracting proteins from the tuber and separating them electrophoretically.

Potato variety FL1900 has the following morphologic and other characteristics.

| VARIETY DESCRIPTION INFORMATION | |
|---|---|
| 1. Classification: *Solanum Tuberosum* L. | |
| 2. Plant characteristics: (Observed at beginning of bloom) | |
| Growth habit: | Semi-erect (30°–45° with ground) |
| Type: | Intermediate |
| Maturity (Days after planting - DAP): | 105 |
| 3. Stem Characteristics: (Observed at early first bloom) | |
| Stem (anthocyanin coloration): | Strong |
| Stem (wings): | Medium |
| 4. Leaf Characteristics: (Observed fully developed leaves located in the middle one-third of plant): | |
| Leaf (color): | Olive green/ 137A RHS |
| Leaf (silhouette): | Open |
| Petioles (anthocyanin coloration): | Weak |
| Terminal leaflet (shape): | Medium ovate |
| Terminal leaflet (shape of tip): | Acuminate |
| Terminal leaflet (shape of base): | Cordate |
| Terminal leaflet (margin waviness): | Medium |
| Primary leaflets (average pairs): | 3 |
| Primary leaflets (shape): | Medium ovate |
| Primary leaflets (shape of base): | Cordate |
| Number of leaflets (secondary and tertiary): | 16–20 |
| 5. Inflorescence Characteristics: | |
| Closed flower bud (intensity of anthocyanin): | Medium |
| Corolla (shape): | Pentagonal |

-continued

VARIETY DESCRIPTION INFORMATION

| | |
|---|---|
| Corolla (inner surface color): | Violet/88B RHS |
| Corolla size: | 35 mm - medium |
| Calyx (anthocyanin coloration): | Medium |
| Anthers (shape): | Narrow cone |
| Stigma (shape): | Capitate |
| Stigma (color): | Olive green/137A RHS |
| 6. Tuber Characteristics: | |
| Skin (predominant color): | Brown/199B RHS |
| Skin (texture): | Netted |
| Tuber (shape): | Round-Oval |
| Tuber (thickness): | Slightly flattened |
| Tuber eyes (depth): | Shallow |
| Tuber (primary flesh color): | White/155A RHS |
| Tuber (prominence of eyebrows): | Not prominent |
| Tuber (number per plant): | Medium (8–15) |
| 7. Reaction to Diseases: | |
| Bacterial ring rot foliar reaction | Susceptible |
| Bacterial ring rot tuber reaction | Susceptible |
| Late blight *Phytophthora infestans* | Highly susceptible |
| PVY | Highly susceptible |
| 8. Reaction to Pests: | |
| Golden nematode *Globodera rostochiensis* | Resistant |

Persons of ordinary skill in the art will recognize that when the term potato plant is used in the context of the present invention, this also includes derivative varieties that retain the essential distinguishing characteristics of FL1900, such as a Single Gene Converted plant of that variety or a transgenic derivative having one or more value-added genes incorporated therein (such as herbicide or pest resistance. Backcrossing methods can be used with the present invention to improve or introduce a characteristic into the variety. The term backcrossing as used herein refers to the repeated crossing of a hybrid progeny back to the recurrent parents. The parental potato plant which contributes the gene for the desired characteristic is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the single gene transferred from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified, substituted or supplemented with the desired gene from the nonrecurrent parent, while retaining essentially all of the rest of the desired genes, and therefore the desired physiological and morphological constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Likewise, transgenes can be introduced into the plant using any of a variety of established recombinant methods well-known to persons skilled in the art, such as: Gressel, 1985, Biotechnologically Conferring Herbicide Resistance in Crops: The Present Realities, In Molecular Form and Function of the plant Genome, L van Vloten-Doting, (ed.), Plenum Press, New York; Huftner, S. L., et al., 1992, Revising Oversight of Genetically Modified Plants. *Bio/Technology*; Klee, H., et al., 1989, Plant Gene Vectors and Genetic Transformation: Plant Transformation Systems Based on the use of *Agrobacterium tumefaciens, Cell Culture and Somatic Cell Genetics of Plants*; Koncz, C., et al.,1986, The Promoter of $T_L$-DNA Gene 5 Controls the Tissue-Specific Expression of Chimeric Genes Carried by a Novel Type of *Agrobacterium* Binary Vector; *Molecular and General Genetics*; Lawson, C., et al., 1990, Engineering Resistance to Mixed Virus Infection in a Commercial Potato Cultivar: Resistance to Potato Viruses X and Potato Virus Y in Transgenic Russet Burbank, *Bio/Technology*; Mitsky, T. A., et al., 1996, Plants Resistant to Infection by PLRV. U.S. Pat. No. 5,510,253; Newell, C. A., et al., 1991, *Agrobacterium*-mediated transformation of *Solanum tuberosum* L. Cv. Russet Burbank, *Plant Cell Reports*; Perlak, F. J., et al., 1993, Genetically Improved Potatoes: Protection from Damage by Colorado Potato Beetles, *Plant Molecular Biology*; all of which are specifically incorporated herein by reference.

Many single gene traits have been identified that are not regularly selected for in the development of a new variety but that can be improved by backcrossing and genetic engineering techniques. Single gene traits may or may not be transgenic, examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. These genes are generally inherited through the nucleus. Several of these single gene traits are described in U.S. Pat. No. 5,500,365, U.S. Pat. No. 5,387,756, U.S. Pat. No. 5,789,657, U.S. Pat. No. 5,503,999, U.S. Pat. No. 5,589,612, U.S. Pat. No. 5,510,253, U.S. Pat. No. 5,304,730, U.S. Pat. No. 5,382,429, U.S. Pat. No. 5,503,999, U.S. Pat. No. 5,648,249, U.S. Pat. No. 5,312,912, U.S. Pat. No. 5,498,533, U.S. Pat. No. 5,276,268, U.S. Pat. No. 4,900,676, U.S. Pat. No. 5,633,434 and U.S. Pat. No. 4,970,168, the disclosures of which are specifically hereby incorporated by reference.

DEPOSIT INFORMATION

A deposit of the tuber of Potato Cultivar FL 1900 for Frito-Lay, Inc., disclosed above and recited in the appended claims have been made with the American Type Culture Collection (ATCC), 10801 University Boulevard, Manassas, Va. 20110. The date of deposit was Mar. 3, 2004. The deposit of 25 vials of tubers were taken from the same deposit maintained by Frito-Lay, Inc., since prior to the filing date of this application. All restrictions upon the deposit have been removed, and the deposit is intended to meet all of the requirements of 37 C.F.R. §1.801–1.809. The ATCC accession No. is PTA-5842. The deposit will be maintained in the depository for a period of 30 years, or 5 years after the last request, or for the effective life of the patent, whichever is longer, and will be replaced as necessary during that period.

Hereinabove has been set out a new variety of potato, *Solanum tuberosum*, designated as FL1900, including its physical characteristics and qualities by way of illustration and example for purposes of clarity and understanding. It will be obvious that variations are possible within the scope of this invention, as limited only by the scope of the appended claims.

What is claimed is:

1. A potato tuber or part of a tuber of potato variety FL1900, representative tubers having been deposited under ATCC Accession No. PTA-5842.

2. A potato plant or its parts produced by growing the tuber or part of the tuber of claim 1.

3. Pollen of the plant of claim 2.

4. An ovule of the plant of claim 2.

5. A potato plant having all of the physiological and morphological characteristics of the plant of claim 2.

6. Tissue culture of the plant of claim 2.

7. A potato plant regenerated from the tissue culture of claim 6 wherein said regenerated potato plant has all of the physiological and morphological characteristics of a potato plant grown from a potato tuber and having ATCC Accession No. PTA-5842.

8. A method for producing a hybrid potato seed comprising crossing a first potato plant with a second potato plant and harvesting the resultant hybrid potato seed, wherein said first or second parent potato plant or both said first and second potato plant is the potato plant of claim 2.

9. The potato plant, or parts thereof, of claim 5, wherein the plant or parts thereof have been transformed so that its genetic material contains one or more transgenes operably linked to one or more promoter.

10. A method for producing a potato plant that contains in its genetic material one or more transgenes, comprising crossing the potato plant of claim 9 with either a second plant of another potato variety or a non-transformed potato plant of the potato variety FL1900, so that the genetic material of the progeny that result from the cross contains the transgene(s) operably linked to a promoter.

11. A method for developing a potato plant in a potato plant breeding program using plant breeding techniques which include using a potato plant, or its parts, as the source of plant breeding material wherein the source of the plant breeding material is FL1900.

* * * * *